United States Patent
Nakada et al.

(10) Patent No.: US 6,770,036 B2
(45) Date of Patent: Aug. 3, 2004

(54) APPARATUS FOR MEASURING ACTIVITY OF AUTONOMIC NERVE

(75) Inventors: Masato Nakada, Asaka (JP); Toshiaki Sasaki, Tokyo (JP)

(73) Assignee: Tanita Corporation, Tokyo (JP)

(*) Notice: Subject to any disclaimer, the term of this patent is extended or adjusted under 35 U.S.C. 154(b) by 166 days.

(21) Appl. No.: 10/136,400

(22) Filed: May 2, 2002

(65) Prior Publication Data

US 2002/0169365 A1 Nov. 14, 2002

(30) Foreign Application Priority Data

May 8, 2001 (JP) ........................................ 2001-137572

(51) Int. Cl.[7] .................................................. A61B 5/00
(52) U.S. Cl. ...................................... 600/485; 600/500
(58) Field of Search ................................. 600/485, 800, 600/503, 508

(56) References Cited

U.S. PATENT DOCUMENTS

| | | | | |
|---|---|---|---|---|
| 4,896,675 A | * | 1/1990 | Ohsuga et al. | 600/484 |
| 5,178,235 A | | 1/1993 | Montalvo, III et al. | |
| 5,682,901 A | | 11/1997 | Kamen | |
| 5,830,148 A | * | 11/1998 | Inukai et al. | 600/481 |
| 6,358,201 B1 | * | 3/2002 | Childre et al. | 600/300 |
| 6,482,163 B2 | * | 11/2002 | Oka et al. | 600/481 |
| 6,553,763 B1 | * | 4/2003 | Callas et al. | 60/605.2 |

FOREIGN PATENT DOCUMENTS

| | | |
|---|---|---|
| JP | 10-005184 | 1/1998 |
| JP | 10-137228 | 5/1998 |
| JP | 11-151231 | 6/1999 |
| JP | 11-155845 | 6/1999 |
| JP | 11-314534 | 11/1999 |
| JP | 2000-166879 | 6/2000 |
| JP | 2000-210290 | 8/2000 |

* cited by examiner

*Primary Examiner*—Robert L. Nasser
(74) *Attorney, Agent, or Firm*—McDermott Will & Emery LLP

(57) ABSTRACT

Disclosed is an apparatus for measuring an activity of autonomic nerve, comprising: a sympathetic nerve activity measuring unit; a parasympathetic nerve activity measuring unit; a memory unit; and an evaluation unit. According to the present invention the sympathetic nerve activity measuring unit measures an activity of the sympathetic nerve and the parasympathetic nerve activity measuring unit measures an activity of the parasympathetic nerve antagonistically functioning with the sympathetic nerve. The memory unit stores reference data acting as the criterion for comparing with relation between psychosomatic conditions based on the activity of the sympathetic nerve and the activity of the parasympathetic nerve. The evaluation unit compares measurement data representing the activity of the sympathetic nerve measured by said sympathetic nerve activity measuring unit and the activity of the parasympathetic nerve measured by said parasympathetic nerve activity measuring unit with said reference data stored in said memory unit for evaluating the relation between psychosomatic conditions.

5 Claims, 5 Drawing Sheets

APPARATUS FOR MEASURING ACTIVITY OF AUTONOMIC NERVE

BACKGROUND OF THE INVENTION

1. Field of the Invention

The present invention relates to an apparatus for measuring an activity of autonomic nerve that is capable of evaluating the relation between psychosomatic conditions of a person based on the activity of autonomic nerve consisting of sympathetic nerve and parasympathetic nerve.

2. Prior Art

In the past an activity of autonomic nerve has been studied and various types of measurement techniques have been developed. Among those, there have been proposed a method for evaluating comfortableness obtained from a massage (see TOKUKAI 2000-210290); and an apparatus for evaluating stiffness in the shoulder (see TOKUKAI 2000-166879). Those method and apparatus can objectively evaluate the comfortableness and the stiffness in the shoulder as the psychosomatic condition of a person based on the activities of sympathetic nerve and parasympathetic nerve.

Those method and apparatus in the prior art, however, are simply arranged to one-dimensionally evaluate the psychosomatic condition of a person by getting only the comfortableness or only the stiffness in the shoulder.

In view of the above, an object of the present invention is to eliminate the problems in the prior art, as described above, and to provide an improved apparatus for measuring an activity of autonomic nerve that is capable of multi-dimensionally evaluating the psychosomatic conditions of a person.

SUMMARY OF THE INVENTION

To attain such object, the present invention provides an apparatus for measuring an activity of autonomic nerve, comprising: a sympathetic nerve activity measuring unit; a parasympathetic nerve activity measuring unit; a memory unit; and an evaluation unit, whereby said sympathetic nerve activity measuring unit measures an activity of the sympathetic nerve, said parasympathetic nerve activity measuring unit measures an activity of the parasympathetic nerve antagonistically functioning with the sympathetic nerve, said memory unit stores reference data acting as the criterion for comparing with relation between psychosomatic conditions based on the activity of the sympathetic nerve and the activity of the parasympathetic nerve, and said evaluation unit compares measurement data representing the activity of the sympathetic nerve measured by said sympathetic nerve activity measuring unit and the activity of the parasympathetic nerve measured by said parasympathetic nerve activity measuring unit with said reference data stored in said memory unit for evaluating the relation between psychosomatic conditions. According to the present invention the activity of the sympathetic nerve is measured by the sympathetic nerve activity measuring unit, and the activity of the parasympathetic nerve is measured by the parasympathetic nerve activity measuring unit. Then, the measurement data representing the activities of the sympathetic nerve and parasympathetic nerve is compared in the evaluation unit with the reference data stored in the memory unit for evaluating the relation between psychosomatic conditions. In other words, evaluation of the relation between psychosomatic conditions allows the multi-dimensional seizing of the psychosomatic conditions.

According to one embodiment of the present invention the apparatus further comprises a display unit on which the relation between psychosomatic conditions evaluated by said evaluation unit is displayed. Displaying the relation between psychosomatic conditions on the display unit makes possible to visually recognize and clearly understand the psychosomatic conditions.

According to another embodiment of the present invention the display unit multi-dimensionally displays the relation between psychosomatic conditions evaluated by said evaluation unit. Displaying multi-dimensionally the relation between psychosomatic conditions on the display unit also makes possible to visually recognize and clearly understand the psychosomatic conditions.

According to further embodiment of the present invention the display unit divides the relation between psychosomatic conditions into sections around the center point where said measurement data is matched with the reference data. Therefore, the relation between the psychosomatic conditions is displayed in each of the directions around the center point. Thus, the direction or tendency of the psychosomatic condition as to whether it is in exasperation or in inhibitory can be understood.

According to yet further embodiment of the present invention the display unit classifies the relation between psychosomatic conditions by color. This can facilitate identification and understanding of the relation between psychosomatic conditions.

BRIEF DESCRIPTION OF THE DRAWINGS

Now the present invention will be described in more detail with reference to the drawings, in which:

FIG. 5 is a view showing an additional example of the display in which

DESCRIPTION OF THE PREFERRED EMBODIMENTS

Figure 1:
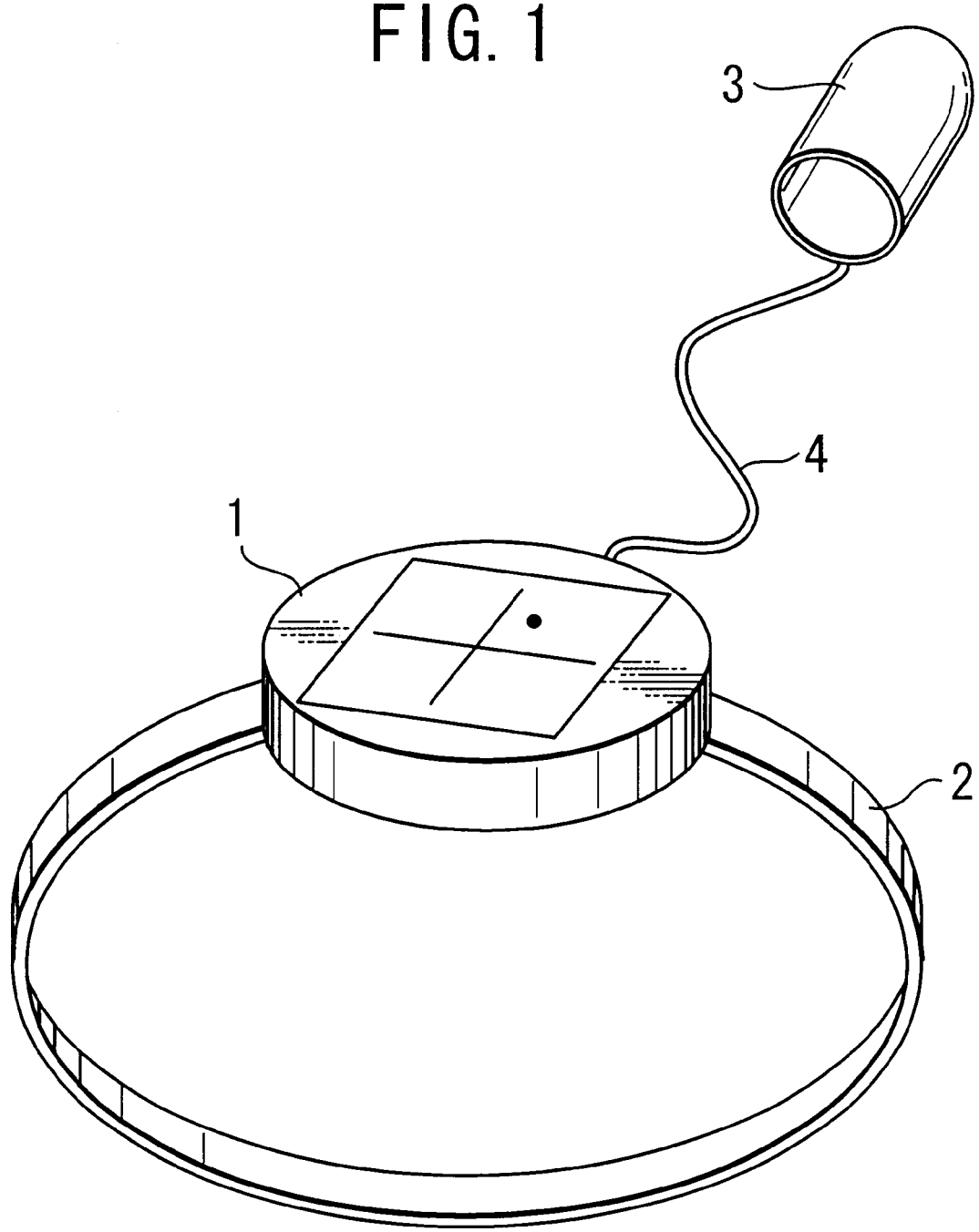
FIG. 1 is a schematic perspective view illustrating an apparatus for measuring an activity of autonomic nerve according to one embodiment of the present invention.
Figure 2:
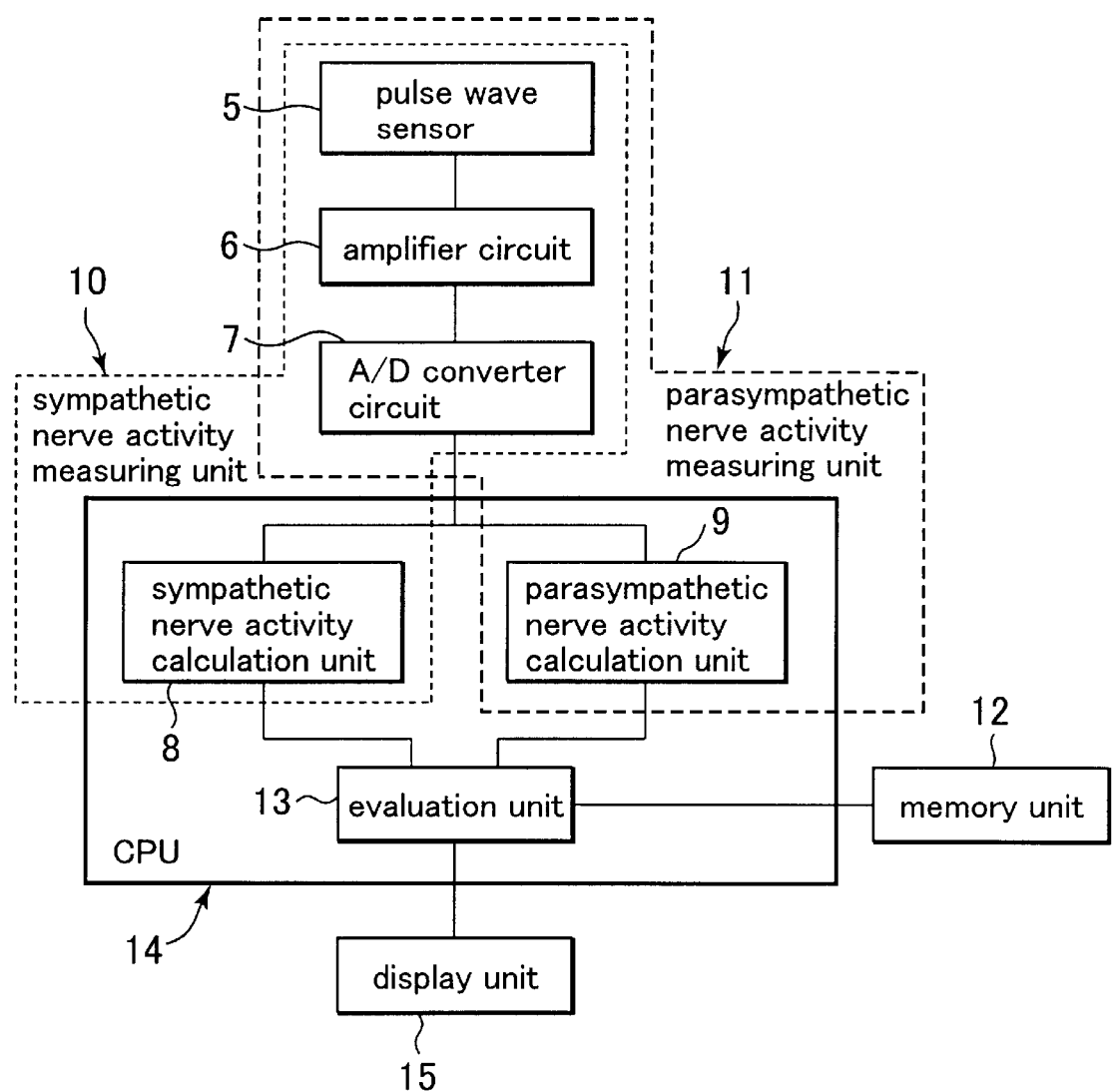
FIG. 2 is a block diagram showing a configuration of the apparatus in FIG. 1.

FIG. 1 is a schematic perspective view illustrating an apparatus for measuring an activity of autonomic nerve according to one embodiment of the present invention, and FIG. 2 is a block diagram showing a configuration of such apparatus. The apparatus of the present invention comprises a body portion 1, a band 2 connected to the body portion 1 and a fingerstall-like detector 3 connected to the body portion 1 via a lead wire 4.

The band 2 is wrapped around a wrist of a person to be measured for holding the body portion 1 of the apparatus. The detector 3 includes a pulse wave sensor 5 known in the art.

The body portion 1 of the apparatus includes an amplifier circuit 6 for amplifying a pulse wave signal detected by the pulse wave sensor 5; an A/D converter circuit 7 for converting an analogue signal output from the amplifier circuit 6 into a digital signal; a sympathetic nerve activity calculation unit 8 for calculating an activity of sympathetic nerve based on the digital signal from the A/D converter circuit 7; and a parasympathetic nerve activity calculation unit 9 for calculating an activity of parasympathetic nerve based on the digital signal from the A/D converter circuit 7.

The amplifier circuit 6, the A/D converter circuit 7 and the sympathetic nerve activity calculation unit 8 within the body portion 1, together with the pulse wave sensor 5 in the detector 3, form a sympathetic nerve activity measuring unit 10 for measuring the activity of sympathetic nerve. In addition, the amplifier circuit 6, the A/D converter circuit 7 and the parasympathetic nerve activity calculation unit 9 within the body portion 1, together with the pulse wave sensor 5 in the detector 3, form a parasympathetic nerve activity measuring unit 11 for measuring the activity of parasympathetic nerve antagonistically functioning with the sympathetic nerve.

The body portion 1 of the apparatus further includes a memory unit 12 and an evaluation unit 13. The memory unit 12 stores reference data acting as the criterion for comparing with relation between psychosomatic conditions based on the activity of the sympathetic nerve and the activity of the parasympathetic nerve. The evaluation unit 13 compares measurement data representing the activity of the sympathetic nerve measured by the sympathetic nerve activity measuring unit 10 and the activity of the parasympathetic nerve measured by the parasympathetic nerve activity measuring unit 11 with the reference data stored in the memory unit 12 for evaluating the relation between psychosomatic conditions.

The sympathetic nerve activity calculation unit 8, the parasympathetic nerve activity calculation unit 9 and the evaluation unit 13 within the body unit 1 are implemented by a CPU 14.

Furthermore, a display unit 15 for displaying the relation between psychosomatic conditions and the like evaluated by the evaluation unit 13 is mounted on the body portion 1 at the outer side thereof.

Figure 3:
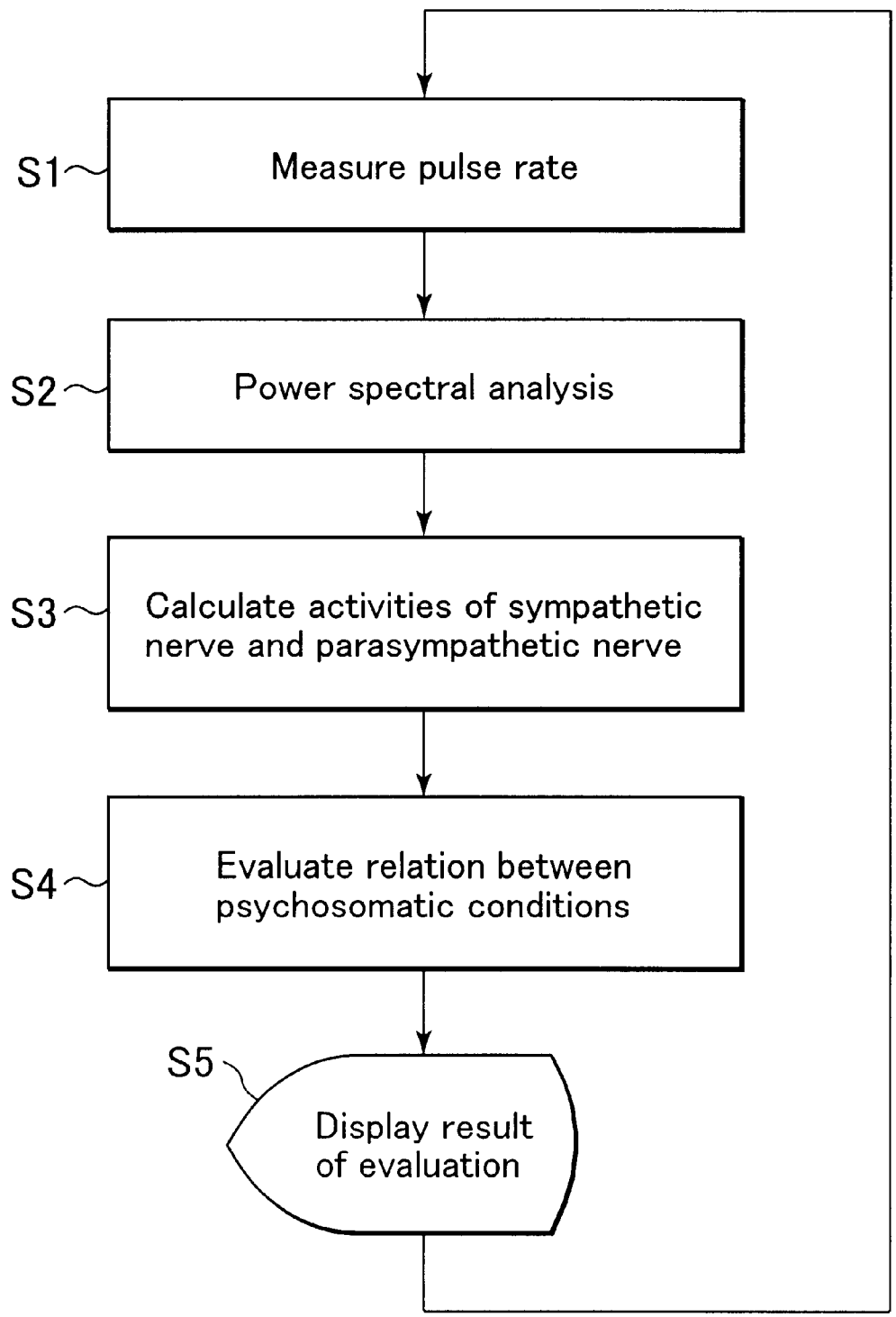
FIG. 3 is a flow chart for explaining an operation of the apparatus.

Now, an operation of the apparatus for measuring the activity of autonomic nerve according to the present invention will be described in detail with reference to a flow chart of FIG. 3.

First of all, according to prior art pulse rate measuring technique, the band 2 of the apparatus for measuring the activity of autonomic nerve according to the present invention is wrapped around the wrist of a person to be measured for holding the body portion 1 of the apparatus thereon. Then the fingerstall-like detector 3 is mounted on an index finger of the person to be measured. The pulse wave sensor 5 included in the detector 3 detects the pulse wave of the person to produce the detected pulse wave signal, which is then amplified by the amplifier circuit 6. The amplified pulse wave signal is then converted in the A/D converter circuit 7 into the digital signal (Step S1).

Thereafter, in the sympathetic nerve activity calculation unit 8 and the parasympathetic nerve activity calculation unit 9, any change in pulse rate is derived based on "R—R" interval of the A/D converted pulse wave signal. Then, a power spectral analysis is performed using first Fourier transformation and the like (Step S2).

Then, in the parasympathetic nerve activity calculation unit 9, the peak value "[HF]me" in strength of the signal within the power spectral analyzed high frequency band is specified to determine the activity of parasympathetic nerve. In addition, in the sympathetic nerve activity calculation unit 8, the peak value "[HF]me" in strength of the signal within the power spectral analyzed high frequency band and the peak value "[LF]me" in strength of the signal within the low frequency band are specified for calculation of "[LF/HF]me" to determine the activity of sympathetic nerve (Step S3).

It is assumed, here, that the activity of the parasympathetic nerve is represented by a peak value in strength of the signal within the high frequency band, while the activity of the sympathetic nerve is represented by a peak value in strength of the signal within the low frequency band divided by a peak value in strength of the signal within the high frequency band. Such values are adopted because they are considered to properly reflect the parasympathetic nerve and the sympathetic nerve, based on an examination of results of various studies that have been published. However, another kind of values may be adopted if they properly reflect the parasympathetic nerve and the sympathetic nerve.

Then, in the evaluation unit 13, the measurement data representing the activity of the parasympathetic nerve and the activity of the sympathetic nerve derived in Step S3 ([HF]me and [LF/HF]me) is compared with the reference data ([HF]st and [LF/HF]st) stored in the memory unit 12, and the evaluation of the relation between psychosomatic conditions is performed according to the result of comparison in the following manner:

If the result of comparison is [HF]me>[HF]st and [LF/HF]me>[LF/HF]st then there is a tendency of increased vivacity of the person and the tendency of tension of the person is evaluated as to whether it is higher or lower, based on the magnitude of difference between the values compared. If the result of comparison is [HF]me<[HF]st and [LF/HF]me<[LF/HF]st then there is a tendency of decreased vivacity and the tendency of tension of the person is evaluated in the same manner. If the result of comparison is [HF]me<[HF]st and [LF/HF]me>[LF/HF]st then there is a tendency of increased tension of the person and the tendency of vivacity of the person is evaluated as to whether it is higher or lower, based on the magnitude of difference between the values compared. If the result of comparison is [HF]me>[HF]st and [LF/HF]me<[LF/HF]st then there is a tendency of decreased tension and the tendency of vivacity is evaluated in the same manner (Step S4).

It is noted, here, that two psychosomatic conditions, i.e., "vivacity" and "tension" are used in step S4, but other psychosomatic conditions may be used. In addition, more than two psychosomatic conditions may be used. It is assumed, here, that the psychosomatic condition means "psyche (or mind)" or "soma (or body)" condition or both of them.

The reference data acting as the criterion used in step S4 for comparing with the measurement data is selected among those data including the predetermined data that have been derived from the various kinds of data, the data of a person to be measured while he is ordinarily in rest, the normal data derived by averaging the past measurement data of a person to be measured, and the like.

The balance between the sympathetic nerve and the parasympathetic nerve commonly changes according to the circadian rhythm, which may cause any shift of a reference point or an intersection between the reference data of the activity of the sympathetic nerve and that of the activity of the parasympathetic nerve. Assuming that a person continues to keep the healthy condition without any stress, for instance, it is considered that the balance between the sympathetic nerve and the parasympathetic nerve changes in curvilinear according to the circadian rhythm. In such case it is only necessary that the circadian rhythm for the balance between the sympathetic nerve and the parasympathetic nerve of the person is measured, thereby providing the reference data whose reference point is shifted on the balance curve that changes in curvilinear according to the circadian rhythm. Such balance curve may be produced in several ways, based on the average of the data measured for longer time period, the expected values produced by sampling several points within a day, and the like.

Figure 4:
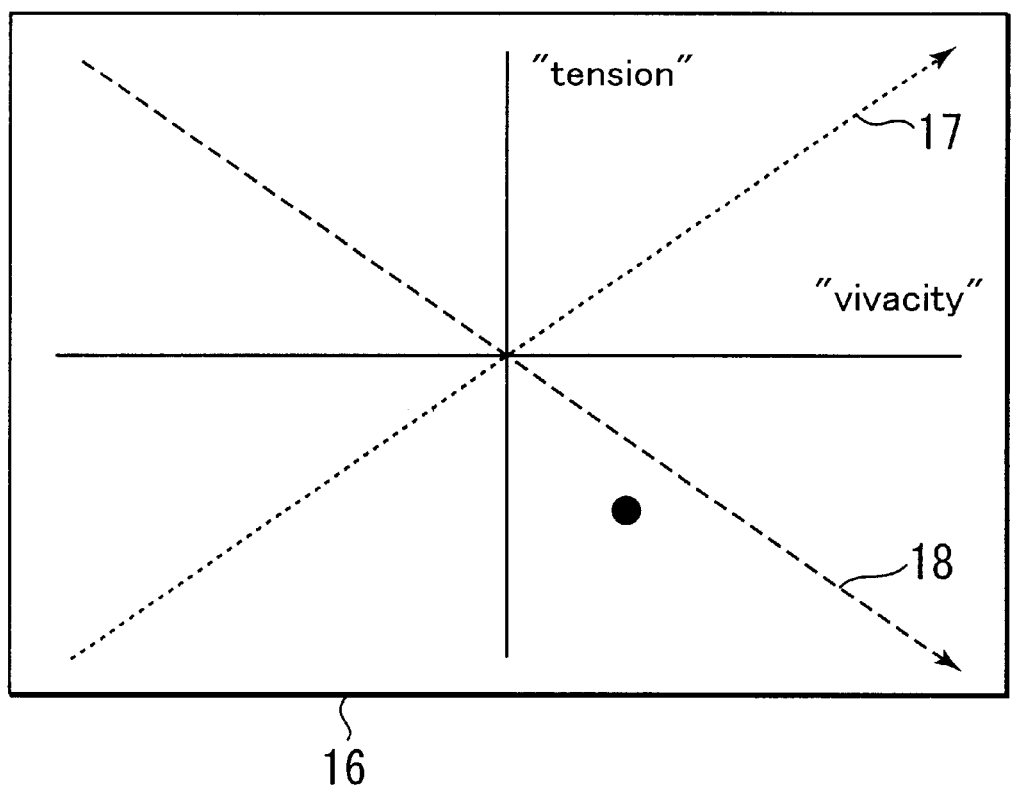
FIG. 4 is a view showing an example of a display on a display unit of the apparatus.

Referring to FIG. 4 that illustrates one example of a screen 16 of the display unit 15, the "vivacity" is plotted on the horizontal axis and the "tension" is plotted on the vertical axis. The both horizontal and vertical axes intersect at a position that is defined as the center point where the measurement data is matched with the reference data. The result of evaluation produced by the evaluation unit 13 representing the relation between psychosomatic conditions is displayed on the screen 16 with continuous lighting or flashing (Step S5).

In particular, the result of evaluation produced by the evaluation unit 13 representing the relation between psychosomatic conditions is displayed in such manner that the activity of sympathetic nerve derived by the sympathetic nerve activity calculation unit 8 is represented by a parallel line drawn from a sympathetic nerve activity virtual axis 17 (actually not appeared on the screen) to a parasympathetic nerve activity virtual axis 18 (actually not appeared on the screen), while the activity of parasympathetic nerve derived by the parasympathetic nerve activity calculation unit 9 is represented by a parallel line drawn from the parasympathetic nerve activity virtual axis 18 (actually not appeared on the screen) to the sympathetic nerve activity virtual axis 17 (actually not appeared on the screen), and an intersection of those parallel lines is defined as a point corresponding to the result of evaluation.

It is noted that the result of evaluation may be lighted or flashed with different color depending on the result of relation between psychosomatic conditions. Alternatively, each of sections provided by intersection of two axes may have different color.

As is apparent from the foregoing, the apparatus for measuring an activity of autonomic nerve according to the present invention is operated in such manner that the sympathetic nerve activity measuring unit 10 measures the activity of sympathetic nerve and the parasympathetic nerve activity measuring unit 11 measures the activity of parasympathetic nerve. Then the evaluation unit 13 compares such measurement data with the reference data stored in the memory 12 for evaluating the relation between the psychosomatic conditions. As the result, the psychosomatic conditions can multi-dimensionally be seized.

In the display unit 15, the axes representing the psychosomatic conditions intersect at a position that is defined as the center point where the measurement data is matched with the reference data, and the relation between the psychosomatic conditions at the time of measurement is displayed in each of the directions around the center point. Therefore, the direction or tendency of the psychosomatic condition as to whether it is in exasperation or in inhibitory can be understood.

In addition, the result of evaluation can readily be understood because it may be lighted or flashed with different color depending on the result of relation between the psychosomatic conditions or each of sections provided by intersection of two axes may have different color.

Figure 5A:
FIG. 5A shows a case where the date and time are displayed.
Figure 5B:
FIG. 5B shows a case where the time and pulse rate are displayed.
Figure 5C:
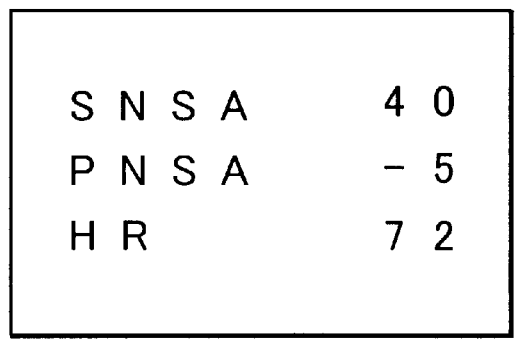
FIG. 5C shows a case where an activity of sympathetic nerve and an activity of parasympathetic nerve are shown together with the pulse rare.

Referring to FIGS. 5A, 5B and 5C that illustrate additional examples of the display, the pulse rate (HR) calculated from the signal in step S1 may be added to the display of the sympathetic nerve activity (SNSA) and the parasympathetic nerve activity (PNSA) with or without the date and time information. Furthermore, what item is displayed may be switched using some switch unit.

In addition, the sympathetic nerve activity measuring unit 10 and the parasympathetic nerve activity measuring unit 11 are not limited to those that have been described in the embodiment of the present invention. For example, the activity of sympathetic nerve or parasympathetic nerve may be measured on the basis of the blood pressure, electrocardiogram, electroencephalogram and the like.

It is apparent from the foregoing that the present invention compares the measurement data with the reference data for evaluating the relation between psychosomatic conditions by the evaluation unit so that the psychosomatic conditions can multi-dimensionally be seized. The result of evaluation given by the evaluation unit is displayed on the display unit by classifying the relation between psychosomatic conditions with different colors, or by dividing the relation between psychosomatic conditions into sections around the center point where the measurement data is matched with the reference data. Therefore, it is possible to visually recognize the direction or tendency of the psychosomatic condition as to whether it is in exasperation or in inhibitory, which can assist multi-dimensional seizing of the psychosomatic conditions.

What is claimed is:

1. An apparatus for measuring an activity of autonomic nerve, comprising:

a detector unit;

a sympathetic nerve activity measuring unit;

a parasympathetic nerve activity measuring unit;

a memory unit; and an evaluation unit, wherein said detector unit detects a pulse wave of a person under test to produce a pulse wave signal, said sympathetic nerve activity measuring unit measures as an activity of the sympathetic nerve "[LF/HF]me" of the peak value "[LF]me" of the strength of the pulse wave signal within a low frequency band divided by the peak value "[HF]me" of the strength of the pulse wave signal within a high frequency band, said parasympathetic nerve activity measuring unit measures as an activity of the parasympathetic nerve the peak value "[HF]me" of the strength of the pulse wave signal within the high high frequency band, said memory unit stores reference data "[HF]st" and "[LF/HF]st", and said evaluation unit compares the activity of the sympathetic nerve "[LF/HF]me" measured by said sympathetic nerve activity measuring unit with the reference data "[LF/HF]st" and the activity of the parasympathetic nerve "[HF]me" measured by said parasympathetic nerve activity measuring unit with the reference data "[HF]st" and, if the result of comparison is "[HF]me">"[HF]st" and "[LF/HF]me">"[LF/HF]st", determines that there is a tendency of increased vivacity of the person under test, and evaluates a tendency of tension of the person as to whether it is higher or lower, based on the magnitude of difference between the values compared, if the result of comparison is "[HF]me"<"[HF]st" and "[LF/HF]me"<"[LF/HF]st", determines that there is a tendency of decreased vivacity of the person and evaluates a tendency of tension of the person as to whether it is higher or lower, based on the magnitude of difference between the values compared, if the result of comparison is "[HF]me"<"[HF]st" and "[LF/HF]me">"[LF/HF]st", determines that there is a tendency of increased tension of the person and evaluates a tendency of vivacity of the person as to whether it is higher or lower, based on the magnitude of difference between the values compared, and if the result of comparison is "[HF]me">"[HF]st" and "[HF]me"<"[HF]st", determines that there is a tendency of decreased tension of the person and evaluates a tendency of vivacity of the person as to whether it is higher or lower, based on the magnitude of difference between the values compared.

2. An apparatus for measuring an activity of autonomic nerve according to claim 1 in which it further comprises a display unit on which the person's state relative to tension and vivacity evaluated by said evaluation unit is displayed.

3. An apparatus for measuring an activity of autonomic nerve according to claim 2 in which said display unit multi-dimensionally displays the person's state relative to tension and vivacity evaluated by said evaluation unit.

4. An apparatus for measuring an activity of autonomic nerve according to claim 3 in which said display unit divides the relation between tension and vivacity into sections around the center point where said measurement data is matched with the reference data.

5. An apparatus for measuring an activity of autonomic nerve according to any one of claims 2 to 4 in which said display unit classifies the relation between tension and vivacity by color.

* * * * *